United States Patent [19]
Fritchie et al.

[11] Patent Number: 6,022,746
[45] Date of Patent: Feb. 8, 2000

[54] ALLOCATION METHOD

[75] Inventors: Patrick P. Fritchie, Southlake, Tex.; Michael T. Glass, Northbrook, Ill.

[73] Assignee: Abbott Laboratories, Abbott Park, Ill.

[21] Appl. No.: 09/041,352

[22] Filed: Mar. 12, 1998

[51] Int. Cl.[7] .................................................. G01N 35/02
[52] U.S. Cl. ............................... 436/50; 436/47; 422/67; 364/528.01
[58] Field of Search .................................. 436/43, 47, 48, 436/50, 55; 422/63, 65, 67; 364/528.01

[56] References Cited

U.S. PATENT DOCUMENTS

| | | | |
|---|---|---|---|
| 5,087,423 | 2/1992 | Ishibashi | 422/67 |
| 5,209,903 | 5/1993 | Kanamori et al. | 422/65 |
| 5,677,188 | 10/1997 | Mitsumaki et al. | 436/47 |
| 5,719,059 | 2/1998 | Mimura et al. | 436/50 |
| 5,757,659 | 5/1998 | Arai et al. | 364/497 |
| 5,876,670 | 3/1999 | Mitsumaki et al. | 422/65 |
| 5,928,952 | 7/1999 | Hutchins et al. | 436/50 |

*Primary Examiner*—Long V. Le
*Attorney, Agent, or Firm*—Mark C. Bach

[57] ABSTRACT

Methods of allocating resources in a system comprising at least two instruments are provided. In one such method, a list of tests to be performed by the system within a reaction vessel is generated. The list includes a number of reaction vessels used in performing each test to be performed by the system in a given time period. The list of tests is sorted according to the number of reaction vessels used in performing each test to be performed by the system in a given time period. A duplication percentage for the tests is determined. The duplication percentage is compared with the sorted list of tests. Resources associated with the tests are duplicated across the at least two instruments based on the comparison of the duplication percentage with the sorted list of tests such that at least one of the tests is performed by at least two of the at least two instruments.

8 Claims, 3 Drawing Sheets

ALLOCATION METHOD

BACKGROUND

The following relates generally to a method of allocating resources in a system. More specifically, the following relates to a method of allocating resources or supplies, such as reagents, disposables and the like, in a medical diagnostic system.

Some medical diagnostic systems include a machine which performs a test on a patient sample, such as blood and the like, to determine health status of the patient. In order to do a large number of tests in a given time period, a number of such machines may be connected to make up the medical diagnostic system. For instance, if one machine can do 200 tests in one hour, then four machines connected together by a common supply of samples could do 800 tests in one hour.

In some instances, once a number of machines are connected together, the number of tests performed may not be as large as possible or as desired. Accordingly, it is desirable to allocate resources or supplies among the connected machines to perform as many tests as reasonably possible in a given time period.

SUMMARY

Methods of allocating resources in a system comprising at least two instruments are provided. In one such method, a list of tests to be performed by the system within a reaction vessel is generated. The list includes a number of reaction vessels used in performing each test to be performed by the system in a given time period. The list of tests is sorted according to the number of reaction vessels used in performing each test to be performed by the system in a given time period. A duplication percentage for the tests is determined. The duplication percentage is compared with the sorted list of tests. Resources associated with the tests are duplicated across the at least two instruments based on the comparison of the duplication percentage with the sorted list of tests such that at least one of the tests is performed by at least two of the at least two instruments.

DETAILED DESCRIPTION OF ILLUSTRATED EMBODIMENTS

For the sake of clarity of understanding, embodiments of an allocation method will be described herein with respect to one particular employment. Specifically, the allocation method will be discussed with respect to a system 10 comprising instruments substantially similar to those disclosed in co-pending U.S. patent applications Ser. Nos. 08/715,924, 08/715,780, now U.S. Pat. No. 5,856,194, 08/878,521, 08/716,079, now U.S. Pat. No. 5,795,784 and 08/816,121, now abandoned. Those applications are assigned to the assignee of the present application and the disclosures thereof are incorporated herein in their entirety by this reference. It is to be remembered that the allocation method can be utilized with other instruments and systems as appropriate. Also, steps comprising the allocation method may be executed in any appropriate order. Furthermore, steps from one method may be combined with steps from another method to arrive at yet more methods.

In a particular employment of the allocation method, the system 10 comprises 4 instruments 12A, 12B, 12C and 12D connected by at least by a common supply of samples. Of course, a system 10 comprising a smaller or greater number of instruments 12A, 12B, 12C and 12D, preferably at least two instruments, can be used, possibly with appropriate modifications to the allocation method. In one exemplary employment, each instrument 12A, 12B, 12C and 12D is capable of performing about 200 tests per hour. Thus, ideally, it is possible that the system 10 could perform about 800 tests in one hour (throughput), the output of the system 10 being the sum of individual outputs of each instrument 12A, 12B, 12C and 12D.

The instruments 12A, 12B, 12C and 12D are operatively connected with a computer or controller 14 having appropriate memory, such as RAM, ROM, EPROM, SRAM and the like, and running suitable routines, such as the allocation method, to monitor and control certain operations of the instruments 12A, 12B, 12C and 12D. The controller 14 is constructed such that the instruments 12A, 12B, 12C and 12D, each alone or in any combination, may be operated and controlled from a central location comprising the controller 14. The controller 14 also includes a user input device, such as a keyboard, a touch-responsive screen, a data carrier, e.g. bar code, reader and the like to enable a user to supply information, commands, etc. to the controller 14 and the instruments 12A, 12B, 12C and 12D.

The each of the instruments 12A, 12B, 12C and 12D is capable of performing a number of tests. These tests can include determinations of a potentially medically significant item of interest, such as HBsAg, HBsAb, AFP, HBcAb, HCV, Estradiol, B-12, B-hCG, CA 19-9, CEA, Ferritin, Folate, Free PSA, FSH, FT 3, FT 4, GHb, HIV 1/2, LH, Progesterone, Prolactin, Testosterone, Total PSA, TSH, TT 3, TT 4 and the like. Because the instruments 12A, 12B, 12C and 12D are connected by a common supply of samples, if each instrument 12A, 12B, 12C and 12D were to perform each test or were to perform a randomly selected subset of those tests, then it is possible that the system 10 might not be able to perform as many tests, i.e. achieve close to maximum throughput, as possible in a given time period.

In order to reduce this possibility, the allocation method is used to selectively allocate tests, along with their associated counterparts, i.e. reagents, disposables, corresponding receptacles in the instruments 12A, 12B, 12C and 12D, and the like, among the instruments 12A, 12B, 12C and 12D comprising the system 10. To provide this reduction, the allocation method determines which tests are to be replicated, to what degree or amount, on which instruments 12A, 12B, 12C and 12D, etc. and how the test work load is to be distributed across which instruments 12A, 12B, 12C and 12D.

Generally, the allocation method can be thought of as comprising multiple sections or portions. These portions can include a manage test distribution list portion, a generate reagent load map portion, a reagent loading portion, a data management portion and a simulate reagent mapping portion. Exemplary embodiments of these portions of the allocation method are now discussed.

MANAGE TEST DISTRIBUTION LIST PORTION

One embodiment of the manage test distribution list portion employed on a given system 10 comprises the step of determining which tests are to be performed by the system 10. Once these tests have been determined, the number of individual runs of each test to be performed in a given time period, such as a 5 hour shift, a 24 hour day, etc., is calculated or derived from experience (history of the system 10 or its environment, i.e. laboratory, hospital, etc.). The tests are sorted based on the number of runs performed in the given time period. This test sorting may be from largest number of runs performed in the given time period to the smallest number of runs performed in the given time period.

A total number of individual runs of all tests performed in the given time period is obtained. A threshold, which may be empirically determined, of the number of individual runs performed in the given time period is set. The threshold represents, for example, a percentage, such as about 30%, of the individual runs of all of the tests to be performed by the system 10 in the given time period. The total number of individual runs of all tests performed in the given time period is compared with the threshold to determine a replication number. For example, referring to TABLES 1 through 3, if the threshold is set at about 30% and the total number of individual runs of all tests performed in the given time period, in this example 5 hours, is 4000, then the replication number is about 1200.

With the replication number being determined, a list of the tests sorted based on the number of runs performed in the given time period is compared with the replication number to determine approximate equivalency between the number of runs performed in the given time period and the replication number. The approximate equivalency indicates which tests, i.e. associated reagents, etc., are to be replicated or distributed across the instruments 12A, 12B, 12C and 12D and to what magnitude. Tests are assigned to each of the instruments 12A, 12B, 12C and 12D while maintaining the number of runs performed in the given time period by each instrument 12A, 12B, 12C and 12D substantially equal. Of course, it is possible for an operator to modify any portion of the allocation method at any suitable time. By using the allocation method, it is possible to achieve approximately 90% or greater percentage of a maximum throughput of the system 10.

Describing the preceding in more detail, to manage a distribution list of the tests across the instruments 12A, 12B, 12C and 12D comprising the system 10, test and number of runs distribution information used by the allocation method are obtained, maintained and updated. An operator can define a particular time period or shift during which the system 10 is to operate. This definition can include operation start and stop times, and may be limited to a 24 hour maximum shift with about 1 minute resolution. A search range, possibly specifying number of shifts, can be defined to allow for further processing. The operator can also define or input test kit sizes, i.e. the number of tests that can be performed with a given kit. It is possible to select an option either to increase throughput or to decrease reagent waste. The operator can request a new reagent load map, store a test distribution list in memory, cancel a current test distribution list, restore a previous test distribution list or print a hard copy of a current or previous test distribution list. The operator can also edit a test distribution list or enter a replication or duplication percentage.

The allocation method may include default values for information that might be entered by an operator. For instance, the default values may include a shift definition of 24 hours (midnight to midnight), a search range of 1 (i.e. last complete shift), a test distribution list corresponding to Test Counts=0 for all tests installed, a smallest available test kit size, and an increase throughput selection.

The allocation method may also include inputs from a software routine, e.g. system 10 software, running on the system 10. These inputs may include configuration data, such as an indication of the tests installed, available test kit sizes and the like, and test data, such as available search range (dates and times), search data (test counts per test), etc.

With those things complete, the allocation method can begin test distribution list processing. Specifically, a previous distribution list (test counts per test per shift) are displayed. The operator inputs defined above are accepted. The allocation routine requests the operator to enter a desired number of runs per test to be performed by the system 10 in a given, operator defined shift and the number of shifts for which this requirement applies. The current test distribution list, comprising average and maximum runs per test per shift, is calculated and displayed. Sometimes, the allocation method can recommend a kit size change. For instance, if current runs per test per shift is 25, then the allocation method might recommend use of a kit which supports 500 runs of the test. The allocation method accepts operator-generated edits to a previous test distribution list and kit sizes. If requested, the allocation method initiates creation of a reagent load map, stores the current test distribution list, cancels the current test distribution list edits, restores the previous test distribution list, and/or prints the current or previous test distribution lists.

Upon processing, the allocation method generates outputs to the operator, the system 10 software and/or to a portion, discussed below, of the allocation method which generates the reagent load map. The outputs provided to the operator may include the previous test distribution list, the current test distribution list-search data comprising both average and maximum test counts per test per shift, a recommended kit size change (if necessary) and any requested print outs, such as a previous test distribution list, a current distribution list, etc. The outputs provided to the system 10 software may include a configuration data request, an available search range request, a search data request, including shift start and stop dates and times, etc. The outputs provided to the portion of the allocation method which generates the reagent load map may include a selected one of an increase throughput or decrease reagent waste option, a test kit size, a current test distribution list, including test counts per test per shift, the threshold, i.e. a percentage of test duplication to increase throughput, etc.

GENERATE REAGENT LOAD MAP PORTION

To generate a reagent load map, it is desirable to determine a theoretical distribution of test reagents and related items among the instruments 12A, 12B, 12C and 12D comprising the system 10. There are no operator inputs and a default setting is that there are 25 reagent pack positions or reagent slots on each of the instruments 12A, 12B, 12C and 12D. This portion of the allocation method accepts as inputs the outputs specified in the preceding paragraph. Also accepted are outputs from the system 10 software. These outputs may include configuration data comprising a number of instruments 12A, 12B, 12C and 12D comprising the system 10, a number of reagent packs per test for all tests installed on the instruments 12A, 12B, 12C and 12D, a number of test tubes or reaction vessels used per test for all tests installed on the instruments 12A, 12B, 12C and 12D, etc.

The allocation method begins processing those inputs. In one embodiment, this processing is completed within a time period less than or equal to about 2 minutes. This processing utilizes one of four possible algorithms or portions: distribute workload, increase throughput, decrease reagent waste and calculate minimum size for partial reagent packs. The first three algorithms listed above assume full reagent packs.

In performing the distribute workload algorithm, it is attempted to find a solution to distribute tests substantially evenly across the instruments 12A, 12B, 12C and 12D. If this attempt were to fail, the operator is notified and then it is attempted to increase a portion of workload processed, such as by using highest volume tests.

In performing the increase throughput algorithm, it is attempted to distribute tests and test tube or reaction vessel utilization substantially evenly across all of the instruments 12A, 12B, 12C and 12D. To do this, the tests utilizing the highest volume of reaction vessels (reaction vessel utilization) are duplicated across the instruments 12A, 12B, 12C and 12D. By duplicating the tests, all associated resources, such as reagents, reaction vessels, calibrators, controls, etc., are duplicated. Specifically, the tests and degree of this duplication are determined by using the threshold, as discussed above. If the duplication percentage cannot be met, the operator is notified.

In performing the decrease reagent waste algorithm, it is attempted to distribute tests and reaction vessel utilization substantially evenly across each of the instruments 12A, 12B, 12C and 12D. Irrespective of which algorithm is used, the algorithm should be repeatable for slightly differing test distribution lists, to decrease reagent kit movements between instruments 12A, 12B, 12C and 12D, and to reduce redundant calibrations. The algorithms assume that the test distribution list test counts are at almost their maximums.

Upon completion of the chosen algorithm, the following outputs are supplied. A configuration data request is sent to the system 10 software, and a theoretical reagent load map, including reagent pack locations, and contents status, i.e. full, minimum, or partial size, empty reagent slots on the instruments 12A, 12B, 12C and 12D, etc.

REAGENT LOADING PORTION

The allocation method also provides an interface with the operator so that the operator can more readily use the reagent load map and thereby facilitate loading of reagents on the instruments 12A, 12B, 12C and 12D. The operator has certain inputs, such as a display view selection and selection of a print routine. Both of these selections can relate to either all of the instruments 12A, 12B, 12C and 12D at once or each of the instruments 12A, 12B, 12C and 12D individually or any other desired combination. Also, an input from a special access operator may be provided. This input may allow for reagent load map generation override.

The outputs from the reagent load map generation portion discussed above are accepted. The system 10 software supplies further information, including, for example, current reagent loading, such as reagent pack locations on each of the instruments 12A, 12B, 12C and 12D, current reagent inventory, such as number of tests in the reagent packs, whether the reagent packs are full packs or partial packs, etc., and calibration status, such as test and lot number for each of the instruments 12A, 12B, 12C and 12D.

During processing, the reagent loading portion of the allocation method compares the theoretical reagent map with the reagent inventory, identifies reagent packs to be removed from the instruments 12A, 12B, 12C and 12D, identifies reagent packs to be loaded on the instruments 12A, 12B, 12C and 12D, identifies additional calibrations to be performed on the instruments 12A, 12B, 12C and 12D and maintains inventory based on the theoretical reagent load map.

The reagent loading portion generates the following outputs for the operator. A display representing a comparison between the theoretical reagent load map and the current inventory is formed. This display may be a graphical and/or numerical chart. Also, both an unload reagent map, showing which reagents are to be unloaded from the instruments 12A, 12B, 12C and 12D, and a reagent load map, showing which reagent are to be loaded onto the instruments 12A, 12B, 12C and 12D are created.

DATA MANAGEMENT PORTION

The data management portion provides system 10 configuration information, and historical results access. There are no operator inputs. The data management portion accepts the outputs from the manage test distribution list portion and the generate reagent load map portion described above. The system 10 software supplies other inputs, including an available search range comprising dates and times, tests installed on the system 10, available test kit sizes, test results, the number of instruments 12A, 12B, 12C and 12D on-line in the system 10, and the number of reagent packs per test for all tests installed.

During processing, the data management portion accepts configuration data requests and test data requests and fulfills data management requests. The data management portion generates outputs, described above, including configuration and test data, supplied to the manage test distribution list portion and the generate reagent load map portion.

SIMULATE REAGENT MAP PORTION

This portion determines throughput for configurations of the system 10 comprising at least two instruments 12A, 12B, 12C and 12D. Inputs to this portion include configuration inputs, such as number of instruments 12A, 12B, 12C and 12D on-line, a shift definition, number of workflow iterations to average simulation results and lab selection. As a default, a "standard" reagent distribution is assumed to simulate allocation method failure. The inputs from the generate reagent load map portion include a theoretical reagent load map including reagent pack locations, whether the reagent packs are full or partial size, and the number and locations of empty reagent slots on each of the instruments 12A, 12B, 12C and 12D. The inputs from the data management portion include lab flow data comprising run counts per test per shift and time of sample arrival data.

During processing, this portion simulates theoretical reagent load maps against corresponding lab flow data for a system including 2, 3 and 4 instruments 12A, 12B, 12C and 12D. Throughput degradation is determined along with sensitivity analysis of percent duplication, number of modules, etc.

After processing, this simulation portion generates a number of simulation outputs. These outputs include throughput degradation, which, in one embodiment, is preferably less than or equal to about 10%, a required duplication percentage ,and any reagent load map limitations.

With the allocation method being generally described above, some examples are given to further elucidate the method. It is to be remembered that the embodiments of the method detailed herein may be modified as appropriate to meet specific needs.

For a given system 10 comprising the instruments 12A, 12B, 12C and 12D, a reagent load map can be generated as follows. The steps performed by the allocation method are shown diagrammatically in the flow chart of FIG. 2.

Figure 1:
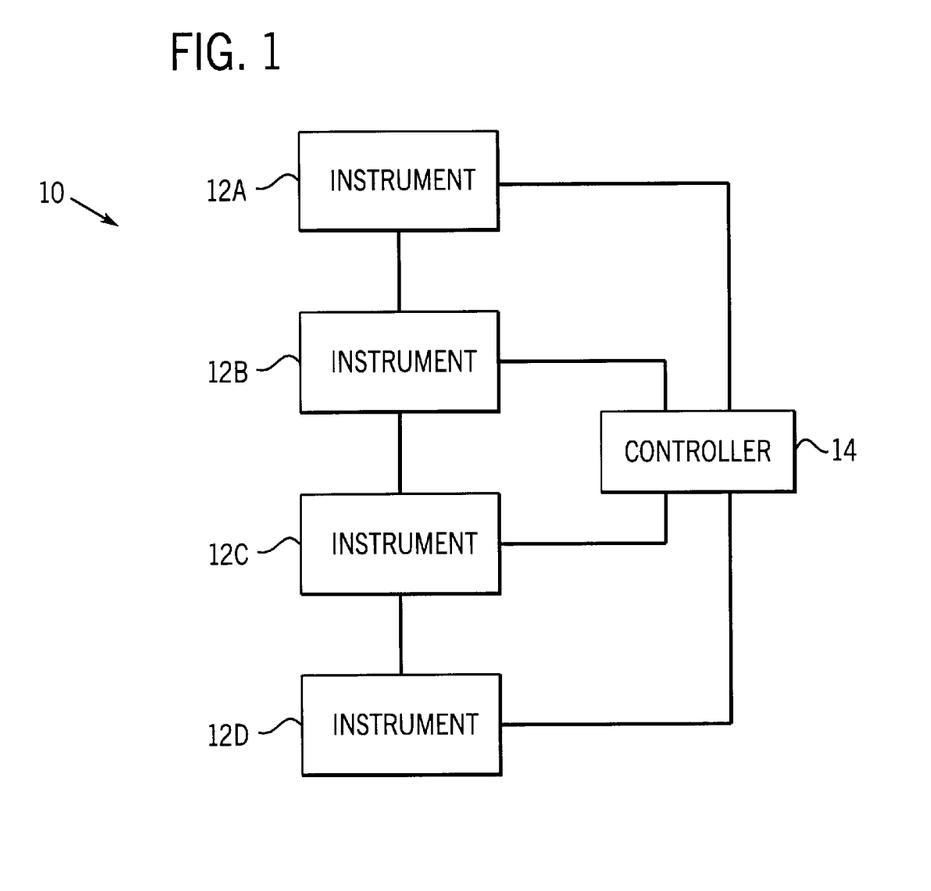
FIG. 1 is a block schematic diagram of a system which may employ an allocation method described herein.
Figure 2:
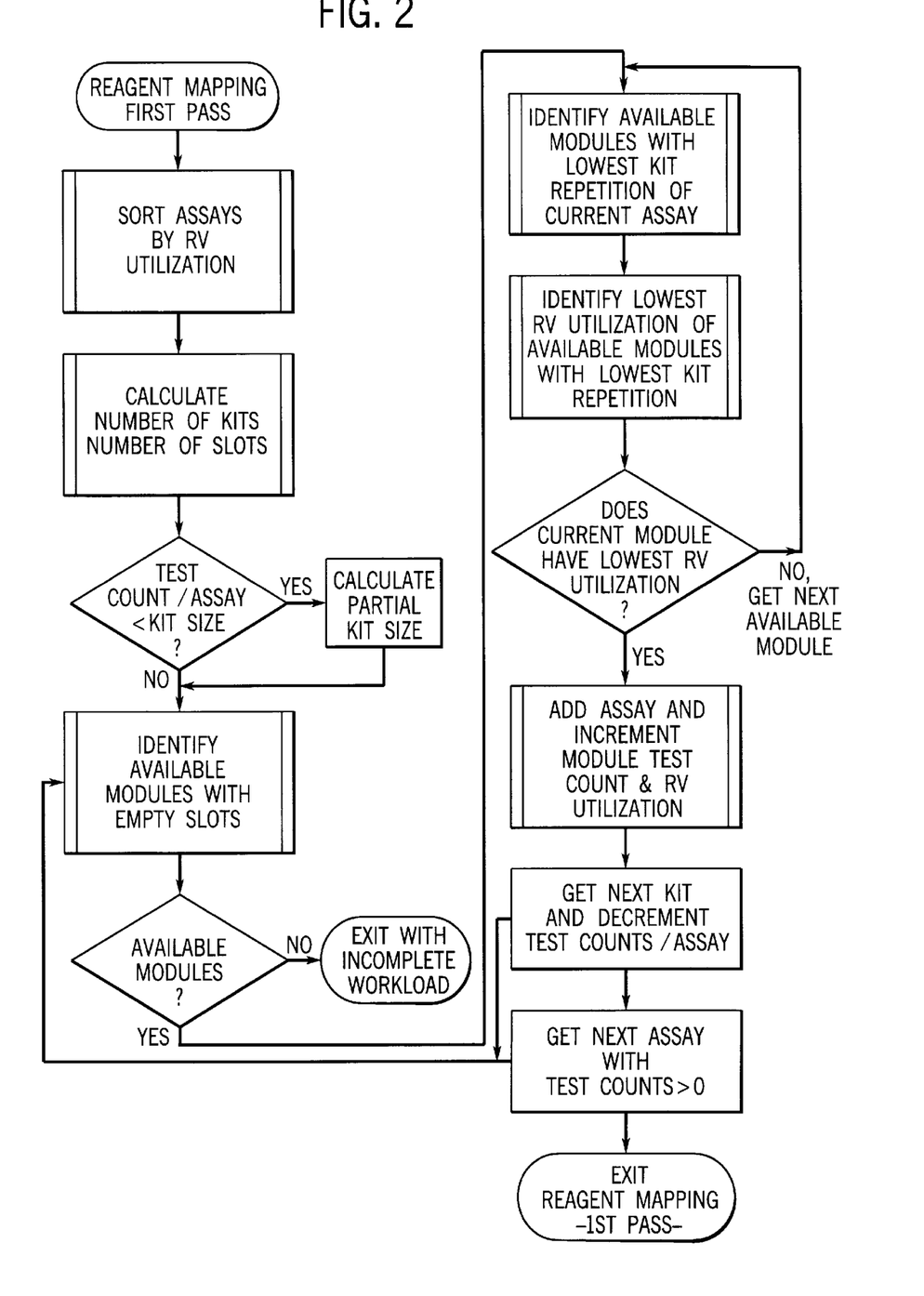
FIG. 2 is a flow chart of a portion of the allocation method.

The processing steps are similar to those described earlier. Specifically, a solution to process test counts or runs, i.e. system 10 workload is attempted. If this attempt fails, it is attempted to increase a portion of the workload processed by the system 10 by using highest volume tests. The operator is notified of an incomplete solution and/or inventory (full reagent packs are assumed). Alternatively, it can be chosen to either increase throughput or to decrease reagent waste. If it were chosen to increase throughput, then it is attempted to distribute tests and reaction vessel utilization substantially evenly across all of the instruments 12A, 12B, 12C and 12D by duplicating highest volume (reaction vessel utilization, the number of reaction vessels used) tests at a percentage less than or equal to the duplication percentage. The operator is warned if throughput cannot be increased, i.e. duplication percentage cannot be met. If it were chosen to decrease reagent waste, then it is attempted to distribute tests and reaction vessel substantially evenly across all of the instruments 12A, 12B, 12C and 12D. In either case, it is assumed that full reagent packs are being used. In another alternative, it may be selected to calculate a minimum size for partial reagent packs. However, as noted earlier, this process should be repeatable for slightly differing test distribution lists to decrease reagent kit movements between instruments 12A, 12B, 12C and 12D, and redundant instrument 12A, 12B, 12C and 12D calibrations. In addition, attempting to calculate a minimum size for partial reagent packs assumes that the test distribution list test counts (runs) are maximums.

The allocation method proceeds to generate a reagent load map in multiple passes. A first iteration or pass attempts to find a solution to process the system's 10 workload. Subsequent passes of the allocation method add additional constraints to optimize throughput, decrease reagent waste, and/or utilize partial reagent packs.

During the first pass, the list of tests performed on the instruments 12A, 12B, 12C and 12D is sorted from highest to lowest volume, i.e. highest to lowest reaction vessel utilization per test per shift. This list also comprises the number of runs of each test, associated reaction vessel utilization, including tests like B-12 which use multiple reaction vessels, an operator defined kit size, a calculated number of kits required (assuming full kits), and a calculated number of reagent slots required (compensating for multiple reagent slot tests like B-12). Examples of such a list are contained in TABLES 1 through 3 below. Each of the TABLES represents a different environment, e.g. laboratory setting, of the system 10.

TABLE 1

| TEST | # OF RUNS | RV UTILIZATION | KIT SIZE | KITS | SPACES |
|---|---|---|---|---|---|
| HBSAg | 1320 | X 1 = 1320 | 500 | 3 | X 1 = 3 |
| HBsAb | 840 | X 1 = 340 | 500 | 2 | X 1 = 2 |
| AFP | 760 | X 1 = 760 | 500 | 2 | X 1 = 2 |
| HBCAb | 520 | X 1 = 520 | 500 | 2 | X 1 = 2 |
| HCV | 480 | X 1 = 480 | 500 | 1 | X 1 = 1 |
| Estradiol | 120 | X 1 = 120 | 500 | 1 | X 1 = 1 |
| B-12 | 0 | X 2 = 0 | 100 | 0 | X 2 = 0 |
| B-hCG | 0 | X 1 = 0 | 100 | 0 | X 1 = 0 |
| CA 19-9 | 0 | X 1 = 0 | 100 | 0 | X 1 = 0 |
| CEA | 0 | X 1 = 0 | 100 | 0 | X 1 = 0 |
| Ferritin | 0 | X 1 = 0 | 100 | 0 | X 1 = 0 |
| Folate | 0 | X 2 = 0 | 100 | 0 | X 2 = 0 |
| Free PSA | 0 | X 1 = 0 | 100 | 0 | X 1 = 0 |
| FSH | 0 | X 1 = 0 | 100 | 0 | X 1 = 0 |
| FT 3 | 0 | X 1 = 0 | 100 | 0 | X 1 = 0 |
| FT 4 | 0 | X 1 = 0 | 100 | 0 | X 1 = 0 |
| GHb | 0 | X 1 = 0 | 100 | 0 | X 1 = 0 |
| HTV ½ | 0 | X 1 = 0 | 100 | 0 | X 1 = 0 |
| LH | 0 | X 1 = 0 | 100 | 0 | X 1 = 0 |
| Progesterone | 0 | X 1 = 0 | 100 | 0 | X 1 = 0 |
| Pralactin | 0 | X 1 = 0 | 100 | 0 | X 1 = 0 |
| Testosterone | 0 | X 1 = 0 | 100 | 0 | X 1 = 0 |
| Total PSA | 0 | X 1 = 0 | 100 | 0 | X 1 = 0 |
| TSH | 0 | X 1 = 0 | 100 | 0 | X 1 = 0 |
| TT 3 | 0 | X 1 = 0 | 100 | 0 | X 1 = 0 |
| TT 4 | 0 | X 1 = 0 | 100 | 0 | X 1 = 0 |
| Totals | 4000 | 4000 | | 11 | 11 |

TABLE 2

| TEST | # OF RUNS | RV UTILIZATION | KIT SIZE | KITS | SPACES |
|---|---|---|---|---|---|
| HBSAg | 240 | X 1 = 240 | 500 | 1 | X 1 = 1 |
| HBsAb | 200 | X 1 = 200 | 500 | 1 | X 1 = 1 |
| AFP | 120 | X 1 = 120 | 500 | 1 | X 1 = 1 |
| HBCAb | 200 | X 1 = 200 | 500 | 1 | X 1 = 1 |
| HCV | 80 | X 1 = 80 | 500 | 1 | X 1 = 1 |
| Estradiol | 40 | X 1 = 40 | 500 | 1 | X 1 = 1 |
| B-12 | 160 | X 2 = 320 | 500 | 1 | X 2 = 2 |
| B-hCG | 80 | X 1 = 80 | 500 | 1 | X 1 = 1 |
| CA 19-9 | 40 | X 1 = 40 | 500 | 1 | X 1 = 1 |
| CEA | 240 | X 1 = 240 | 500 | 1 | X 1 = 1 |
| Ferritin | 280 | X 1 = 280 | 500 | 1 | X 1 = 1 |
| Folate | 80 | X 2 = 160 | 500 | 1 | X 2 = 2 |
| Free PSA | 0 | X 1 = 0 | 100 | 0 | X 1 = 0 |
| FSH | 80 | X 1 = 80 | 500 | 1 | X 1 = 1 |
| FT 3 | 120 | X 1 = 120 | 500 | 1 | X 1 = 1 |
| FT 4 | 280 | X 1 = 280 | 500 | 1 | X 1 = 1 |
| GHb | 200 | X 1 = 200 | 500 | 1 | X 1 = 1 |
| HIV ½ | 80 | X 1 = 80 | 500 | 1 | X 1 = 1 |
| LH | 80 | X 1 = 80 | 500 | 1 | X 1 = 1 |
| Progesterone | 40 | X 1 = 40 | 500 | 1 | X 1 = 1 |
| Prolactin | 80 | X 1 = 80 | 500 | 1 | X 1 = 1 |
| Testosterone | 40 | X 1 = 40 | 500 | 1 | X 1 = 1 |
| Toal PSA | 280 | X 1 = 280 | 500 | 1 | X 1 = 1 |
| TSH | 520 | X 1 = 520 | 500 | 2 | X 1 = 2 |
| TT 3 | 200 | X 1 = 200 | 500 | 1 | X 1 = 1 |
| TT 4 | 240 | X 1 = 240 | 500 | 1 | X 1 = 1 |
| Totals | 4000 | 4240 | | 26 | 28 |

TABLE 3

| TEST | # OF RUNS | RV UTILIZATION | KIT SIZE | KITS | SPACES |
|---|---|---|---|---|---|
| HBSAg | 400 | X 1 = 400 | 500 | 1 | X 1 = 1 |
| HBsAb | 200 | X 1 = 200 | 500 | 1 | X 1 = 1 |
| AFP | 720 | X 1 = 720 | 500 | 2 | X 1 = 2 |
| HBcAb | 160 | X 1 = 160 | 500 | 1 | X 1 = 1 |
| HCV | 240 | X 1 = 240 | 500 | 1 | X 1 = 1 |
| Estradiol | 120 | X 1 = 120 | 500 | 1 | X 1 = 1 |
| B-12 | 0 | X 2 = 0 | 100 | 0 | X 2 = 0 |
| B-hCG | 0 | X 1 = 0 | 100 | 0 | X 1 = 0 |
| CA 19-9 | 0 | X 1 = 0 | 100 | 0 | X 1 = 0 |
| CEA | 1000 | X 1 = 100 | 500 | 2 | X 1 = 2 |
| Ferritin | 0 | X 1 = 0 | 100 | 0 | X 1 = 0 |
| Folate | 0 | X 2 = 0 | 100 | 0 | X 2 = 0 |
| Free PSA | 0 | X 1 = 0 | 100 | 0 | X 1 = 0 |
| FSH | 0 | X 1 = 0 | 100 | 0 | X 1 = 0 |
| FT 3 | 240 | X 1 = 240 | 500 | 1 | X 1 = 1 |
| FT 4 | 240 | X 1 = 240 | 500 | 1 | X 1 = 1 |
| GHb | 0 | X 1 = 0 | 100 | 0 | X 1 = 0 |
| HIV ½ | 80 | X 1 = 80 | 500 | 1 | X 1 = 1 |
| LH | 0 | X 1 = 0 | 100 | 0 | X 1 = 0 |
| Progesterone | 0 | X 1 = 0 | 100 | 0 | X 1 = 0 |
| Prolactin | 0 | X 1 = 0 | 100 | 0 | X 1 = 0 |
| Testosterone | 0 | X 1 = 0 | 100 | 0 | X 1 = 0 |
| Total PSA | 0 | X 1 = 0 | 100 | 0 | X 1 = 0 |
| TSH | 360 | X 1 = 360 | 500 | 1 | X 1 = 1 |
| TT 3 | 120 | X 1 = 120 | 500 | 1 | X 1 = 1 |
| TT 4 | 160 | X 1 = 160 | 500 | 1 | X 1 = 1 |
| Totals | 4000 | 4000 | | 15 | 15 |

With the first pass of reagent mapping complete, creation of the reagent load map begins. Starting at a selected one of the instruments 12A, 12B, 12C and 12D, such as the first one of the instruments 12A, 12B, 12C and 12D encountered by a sample conveyed by the common sample supply, test kits and reaction vessel utilization are correlated to achieve a list of test kits, their test counts or runs, also accounting for partial reagent kits, and for each of the instruments 12A, 12B, 12C and 12D, the total tests performed per shift. An exemplary routine followed is:

```
FOR Number of Tests (with Test Counts 0)
    FOR Remaining Test Counts > 0 (for each test)
        IF Remaining Test Counts per Test < Test Kit Size,
            THEN Calculate Partial Kit Size
        Identify Available Instruments (Empty Reagent slots
        Number of Reagent slots Required for Test)
        IF Available Instruments = 0, THEN EXIT with Incomplete
            Workload Solution
        ELSE
            FOR Number of Available Instruments
                Identify Available Instruments with Lowest Kit
                    Repetition of Current Test
                Identify Lowest Reaction Vessel Utilization of
                    Available Instruments with Lowest Kit Repetition
                IF Current Instrument Reaction Vessel Utilization =
                    Lowest Reaction Vessel Utilization of Available
                    Instruments with Lowest Kit Repetition
                THEN ADD Test kit, increment Instrument Test Count (by
                    Kit Size), and increment Instrument Reaction Vessel
                    Utilization
                ELSE Get Next Available Instrument
        Get Next Kit & decrement Test Counts/Test
Get Next Test
```

Exemplary results of this routine are displayed in TABLES 4, 5 and 6. The results of TABLES 4, 5 and 6 correspond to the data displayed in TABLES 1, 2 and 3, respectively, and show in which reagent slot on which of the instruments 12A, 12B, 12C and 12D a particular reagent for a test is to be loaded, as well as the test name and the number of runs of that test to be performed by a given one of the instruments 12A, 12B, 12C and 12D.

TABLE 4

| SLOT # | INSTRUMENT 12A | INSTRUMENT 12B | INSTRUMENT 12C | INSTRUMENT 12D |
|---|---|---|---|---|
| 1 | HBSAg 500 | HBSAg 500 | HBSAg 320 | HBsAb 500 |
| 2 | AFP 500 | AFP 260 | HBsAg 340 | HBcAb 500 |
| 3 |  | Estradiol 120 | HBCAb 20 |  |
| 4 |  |  | HCV 480 |  |
| 5 |  |  |  |  |
| 6 |  |  |  |  |
| 7 |  |  |  |  |
| 8 |  |  |  |  |
| 9 |  |  |  |  |
| 10 |  |  |  |  |
| 11 |  |  |  |  |
| 12 |  |  |  |  |
| 13 |  |  |  |  |
| 14 |  |  |  |  |
| 16 |  |  |  |  |
| 17 |  |  |  |  |
| 18 |  |  |  |  |
| 19 |  |  |  |  |
| 20 |  |  |  |  |
| 21 |  |  |  |  |
| 22 |  |  |  |  |
| 23 |  |  |  |  |
| 24 |  |  |  |  |
| 25 |  |  |  |  |
| TOTALS | 2/1000 | 3/880 | 4/1160 | 2/1000 |

TABLE 5

| SLOT # | INSTRUMENT 12A | INSTRUMENT 12B | INSTRUMENT 12C | INSTRUMENT 12D |
|---|---|---|---|---|
| 1 | TSH 500 | TSH 20 | B-12 (a) 160 | Ferritin 280 |
| 2 | TT 4 240 | FT 4 280 | B-12 (b) 160 | Total PSA 280 |
| 3 | TT 3 200 | CEA 240 | HBSAg 240 | HBSAb 200 |
| 4 | HIV ½ 80 | GHb 200 | HBcAb 200 | FT 3 120 |
| 5 | Estradiol 40 | Folate (a) 80 | AFP 120 | FSH 80 |
| 6 |  | Folate (b) 80 | B-hCG 80 | Prolactin 80 |
| 7 |  | HCV 80 | LH 80 |  |
| 8 |  | CA 19-9 40 | Testosterone 40 |  |
| 9 |  | Progesterone 40 |  |  |
| 10 |  |  |  |  |
| 11 |  |  |  |  |
| 12 |  |  |  |  |
| 13 |  |  |  |  |
| 14 |  |  |  |  |
| 16 |  |  |  |  |
| 17 |  |  |  |  |
| 18 |  |  |  |  |
| 19 |  |  |  |  |
| 20 |  |  |  |  |
| 21 |  |  |  |  |
| 22 |  |  |  |  |
| 23 |  |  |  |  |
| 24 |  |  |  |  |
| 25 |  |  |  |  |
| TOTALS | 5/1060 | 9/1060 | 3/1030 | 6/1040 |

TABLE 6

| SLOT # | INSTRUMENT 12A | INSTRUMENT 12B | INSTRUMENT 12C | INSTRUMENT 12D |
|---|---|---|---|---|
| 1 | CEA 500 | CEA 500 | AFP 500 | AFP 220 |
| 2 | TSH 360 | FT 3 240 | FT 4 240 | HBsAa 400 |
| 3 | TT 4 160 | HBsAb 200 | HBCAb 160 | HCV 240 |
| 4 |  | HIV ½ 80 | TT 3 120 | Estradiol 120 |
| 5 |  |  |  |  |
| 6 |  |  |  |  |
| 7 |  |  |  |  |
| 8 |  |  |  |  |
| 9 |  |  |  |  |
| 10 |  |  |  |  |
| 11 |  |  |  |  |
| 12 |  |  |  |  |
| 13 |  |  |  |  |
| 14 |  |  |  |  |
| 15 |  |  |  |  |
| 16 |  |  |  |  |
| 17 |  |  |  |  |
| 18 |  |  |  |  |
| 19 |  |  |  |  |
| 20 |  |  |  |  |
| 21 |  |  |  |  |
| 22 |  |  |  |  |
| 23 |  |  |  |  |

TABLE 6-continued

| SLOT # | INSTRUMENT 12A | INSTRUMENT 12B | INSTRUMENT 12C | INSTRUMENT 12D |
|---|---|---|---|---|
| 24 | | | | |
| 25 | | | | |
| TOTALS | 3/1020 | 4/1020 | 4/1020 | 4/980 |

A second pass of the allocation method begins. This second pass is illustrated in the flow chart of FIG. 3.

Figure 3:
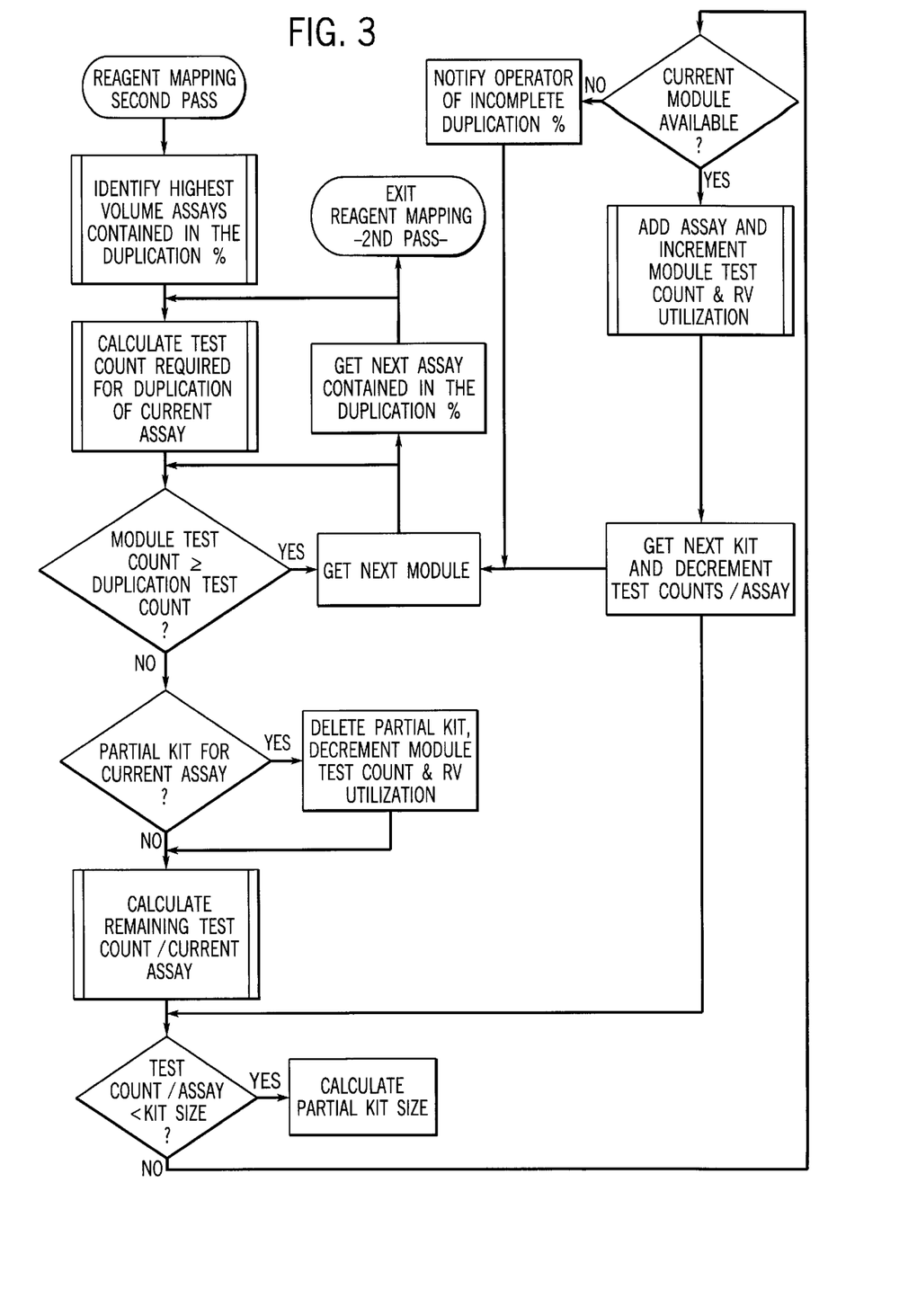
FIG. 3 is a flow chart of another portion of the allocation method.

If the operator selected "Decrease Reagent Waste", then no further action is needed for this second pass. If the operator selected "Increase Throughput", the highest volume, i.e. greatest reaction vessel utilization, tests will be duplicated across the instruments 12A, 12B, 12C and 12D comprising the system 10 to achieve the desired duplication percentage. Using the sorted test distribution list constructed as detailed earlier, the highest volume (reaction vessel utilization) tests meeting duplication percentage of the test distribution list are determined. The number of tests required on each of the instruments 12A, 12B, 12C and 12D, the corresponding number of kits required on each of the instruments 12A, 12B, 12C and 12D (assuming full kits), and the number of reagent slots required on each of the instruments 12A, 12B, 12C and 12D, allowing for multiple reagent slot tests, are calculated.

The duplication level or number is compared with the sorted list of tests. As an example, if the duplication percentage is 30% and if the total number of reaction vessel utilizations per shift is 4000, then 4000 reaction vessel utilizations per shift×0.30=1200 which is the desired duplication level or number of reaction vessel utilizations. If the duplication number occurs "within" a test, i.e. the duplication number is substantially equal to or less than the total number of runs of a test to be performed per shift, then that test will be included on all of the instruments 12A, 12B, 12C and 12D in the system 10. TABLES 7, 8 and 9, corresponding to the data in TABLES 1, 2, 3, 4, 5 and 6, respectively, show further examples highlighting the tests which are duplicated across the instruments 12A, 12B, 12C and 12D.

TABLE 7

| TEST | # OF RUNS | RV UTILIZATION | KIT SIZE | RUNS ON EACH INSTRUMENT | KITS ON EACH INSTRUMENT |
|---|---|---|---|---|---|
| HBSAg | 1320 | X 1 = 1320 | 500 | 330 | X 1 = 3 |
| HBsAb | 840 | X 1 = 840 | 500 | N/A | N/A |
| AFP | 760 | X 1 = 760 | 500 | N/A | N/A |
| HBCAb | 520 | X 1 = 520 | 500 | N/A | N/A |
| HCV | 480 | X 1 = 480 | 500 | N/A | N/A |
| Estradiol | 120 | X 1 = 120 | 500 | N/A | N/A |
| B-12 | 0 | X 2 = 0 | 100 | N/A | N/A |
| B-hCG | 0 | X 1 = 0 | 100 | N/A | N/A |
| CA 19-9 | 0 | X 1 = 0 | 100 | N/A | N/A |
| CEA | 0 | X 1 = 0 | 100 | N/A | N/A |
| Ferritin | 0 | X 1 = 0 | 100 | N/A | N/A |
| Folate | 0 | X 2 = 0 | 100 | N/A | N/A |
| Free PSA | 0 | X 1 = 0 | 100 | N/A | N/A |
| FSH | 0 | X 1 = 0 | 100 | N/A | N/A |
| FT 3 | 0 | X 1 = 0 | 100 | N/A | N/A |
| FT 4 | 0 | X 1 = 0 | 100 | N/A | N/A |
| GHb | 0 | X 1 = 0 | 100 | N/A | N/A |
| HIV 1/2 | 0 | X 1 = 0 | 100 | N/A | N/A |
| LH | 0 | X 1 = 0 | 100 | N/A | N/A |
| Progesterone | 0 | X 1 = 0 | 100 | N/A | N/A |

TABLE 7-continued

| TEST | # OF RUNS | RV UTILIZATION | KIT SIZE | RUNS ON EACH INSTRUMENT | KITS ON EACH INSTRUMENT |
|---|---|---|---|---|---|
| Prolactin | 0 | X 1 = 0 | 100 | N/A | N/A |
| Tetoserone | 0 | X 1 = 0 | 100 | N/A | N/A |
| Total PSA | 0 | X 1 = 0 | 100 | N/A | N/A |
| TSH | 0 | X 1 = 0 | 100 | N/A | N/A |
| TT 3 | 0 | X 1 = 0 | 100 | N/A | N/A |
| TT 4 | 0 | X 1 = 0 | 100 | N/A | N/A |
| Totals | 4000 | 4000 | | N/A | N/A |

TABLE 8

| TEST | # OF RUNS | RV UTILIZATION | KIT SIZE | RUNS ON EACH INSTRUMENT | KITS ON EACH INSTRUMENT |
|---|---|---|---|---|---|
| HBSAg | 240 | X 1 = 240 | 500 | N/A | N/A |
| HBSAb | 200 | X 1 = 200 | 500 | N/A | N/A |
| AFP | 120 | X 1 = 120 | 500 | N/A | N/A |
| HBCAb | 200 | X 1 = 200 | 500 | N/A | N/A |
| HCV | 80 | X 1 = 80 | 500 | N/A | N/A |
| Estradiol | 40 | X 1 = 40 | 500 | N/A | N/A |
| B-12 | 160 | X 2 = 320 | 500 | 40 | 1 |
| B-hCG | 80 | X 1 = 80 | 500 | N/A | N/A |
| CA 19-9 | 40 | X 1 = 40 | 500 | N/A | N/A |
| CEA | 240 | X 1 = 240 | 500 | N/A | N/A |
| Ferritin | 280 | X 1 = 280 | 500 | 70 | 1 |
| Falate | 80 | X 2 = 160 | 500 | N/A | N/A |
| Free PSA | 0 | X 1 = 0 | 100 | N/A | N/A |
| FSH | 80 | X 1 = 80 | 500 | N/A | N/A |
| FT 3 | 120 | X 1 = 120 | 500 | N/A | N/A |
| FT 4 | 280 | X 1 = 280 | 500 | 70 | 1 |
| GHb | 200 | X 1 = 200 | 500 | N/A | N/A |
| HIV 1/2 | 80 | X 1 = 80 | 500 | N/A | N/A |
| LH | 80 | X 1 = 80 | 500 | N/A | N/A |
| Progesterone | 40 | X 1 = 40 | 500 | N/A | N/A |
| Prolactin | 80 | X 1 = 80 | 500 | N/A | N/A |
| Tertosterone | 40 | X 1 = 40 | 500 | N/A | N/A |
| Total PSA | 230 | X 1 = 230 | 500 | N/A | N/A |
| TSH | 529 | X 1 = 520 | 500 | 130 | 1 |
| TT 3 | 200 | X 1 = 200 | 500 | N/A | N/A |
| TT 4 | 240 | X 1 = 240 | 100 | N/A | N/A |
| Totals | 4000 | 4240 | | N/A | N/A |

TABLE 9

| TEST | # OF RUNS | RV UTILIZATION | KIT SIZE | RUNS ON EACH INSTRUMENT | KITS ON EACH INSTRUMENT |
|---|---|---|---|---|---|
| HBSAg | 400 | X 1 = 400 | 500 | N/A | N/A |
| HBsAb | 200 | X 1 = 200 | 500 | N/A | N/A |
| AFP | 720 | X 1 = 720 | 500 | 180 | 1 |
| HBcAb | 160 | X 1 = 160 | 500 | N/A | N/A |
| HCV | 240 | X 1 = 240 | 500 | N/A | N/A |
| Estradiol | 120 | X 1 = 120 | 500 | N/A | N/A |
| B-12 | 0 | X 2 = 0 | 100 | N/A | N/A |
| B-hCG | 0 | X 1 = 0 | 100 | N/A | N/A |
| CA 19-9 | 0 | X 1 = 0 | 100 | N/A | N/A |
| CEA | 1000 | X 1 = 100 | 500 | 250 | 1 |
| Ferritin | 0 | X 1 = 0 | 100 | N/A | N/A |
| Folate | 0 | X 2 = 0 | 100 | N/A | N/A |
| Free PSA | 0 | X 1 = 0 | 100 | N/A | N/A |
| FSH | 0 | X 1 = 0 | 100 | N/A | N/A |
| FT 3 | 240 | X 1 = 240 | 500 | N/A | N/A |
| FT 4 | 240 | X 1 = 240 | 500 | N/A | N/A |
| GHb | 0 | X 1 = 0 | 100 | N/A | N/A |

TABLE 9-continued

| TEST | # OF RUNS | RV UTILIZATION | KIT SIZE | RUNS ON EACH INSTRUMENT | KITS ON EACH INSTRUMENT |
|---|---|---|---|---|---|
| HIV 1/2 | 80 | X 1 = 80 | 500 | N/A | N/A |
| LH | 0 | X 1 = 0 | 100 | N/A | N/A |
| Progesterone | 0 | X 1 = 0 | 100 | N/A | N/A |
| Prolactin | 0 | X 1 = 0 | 100 | N/A | N/A |
| Testoterone | 0 | X 1 = 0 | 100 | N/A | N/A |
| Total PSA | 0 | X 1 = 0 | 100 | N/A | N/A |
| TSH | 360 | X 1 = 360 | 500 | N/A | N/A |
| TT 3 | 120 | X 1 = 120 | 500 | N/A | N/A |
| TT 4 | 160 | X 1 = 160 | 500 | N/A | N/A |
| Totals | 4000 | 4000 | | N/A | N/A |

Starting at a selected one of the instruments 12A, 12B, 12C and 12D, such as the first instrument encountered by a sample transported by the common sample supply, and using the test distribution created above, the test distribution is adjusted as appropriate to achieve the desired duplication of tests across the instruments 12A, 12B, 12C and 12D. The results may be in substantially the same format, i.e comprising a list of test kits, their test run counts (accounting for partial kits), and a number of total runs performed by each of the instruments 12A, 12B, 12C and 12D per shift. An example of a routine for performing these tasks is given below.

```
FOR Number of Tests (identified within the duplication
percentage),
Identify Test Count required for duplication on each of the
instruments 12A, 12B, 12C and 12D
    (Test Count/Current Test/Shift/Number of Instruments 12A,
12B, 12C and 12D)
        FOR Number of Instruments 12A, 12B, 12C and 12D
        IF Test Count/Current Test/Current Instrument
            Test Count required for duplication,
        THEN Get Next Instrument
        ELSE IF a Partial Kit for Current Test exists,
                THEN DELETE Partial Kit for Current Test,
                decrement Instrument Test Count, and
                decrement Instrument RV Utilization
            Calculate Remaining Test Counts/Test
                (Test Count reguired for duplication - Test
                Count/Current Test/Current Instrument)
            FOR Remaining Test Counts 0 (for that test),
                IF Remaining Test Counts/Test < Test Kit
                Size,
                    THEN Calculate New Partial Kit Size
                IF Current Instrument is Available
                    (Empty Reagent slots Number of Reagent
                    slots Required for Test),
                    THEN ADD Test kit, increment Module Test
                    Count (by Kit Size), and increment
                    Instrument RV Utilization
                    ELSE Notify Operator of Incomplete
                    Duplication %
            Get Next Kit & decrement Test Counts/Assay
    Get Next Assay
```

An example of results of these steps are shown in TABLES 10, 11 and 12, which correspond to TABLES 4, 5 and 6.

TABLE 10

| SLOT # | INSTRUMENT 12A | INSTRUMENT 12B | INSTRUMENT 12C | INSTRUMENT 12D |
|---|---|---|---|---|
| 1 | HBSAg 500 | HBSAg 500 | | HBSAb 500 |
| 2 | AFP 500 | AFP 260 | HBSAg 340 | HBCAb 500 |
| 3 | | Estradiol 120 | HBCAb 20 | HBsAg 330 |
| 4 | | | HCV 480 | |
| 5 | | | HBsAg 330 | |
| 6 | | | | |
| 7 | | | | |
| 8 | | | | |
| 9 | | | | |
| 10 | | | | |
| 11 | | | | |
| 12 | | | | |
| 13 | | | | |
| 14 | | | | |
| 15 | | | | |
| 16 | | | | |
| 17 | | | | |
| 18 | | | | |
| 19 | | | | |
| 20 | | | | |
| 21 | | | | |
| 22 | | | | |
| 23 | | | | |
| 24 | | | | |
| 25 | | | | |
| TOTALS | 2/1000 | 3/880 | 4/1170 | 3/1330 |

TABLE 11

| SLOT # | INSTRUMENT 12A | INSTRUMENT 12B | INSTRUMENT 12C | INSTRUMENT 12D |
|---|---|---|---|---|
| 1 | TSH 500 | | B-12 (a) 160 | Ferritin 230 |
| 2 | TT 4 240 | FT 4 280 | B-12 (b) 160 | Total PSA 280 |
| 3 | TT 3 200 | CEA 240 | HBsAg 240 | HBSAb 200 |
| 4 | HIV 1/2 80 | GHb 200 | HBcAb 200 | FT 3 120 |
| 5 | Estradiol 40 | Folate (a) 30 | AFP 120 | FSH 80 |
| 6 | B-12 (a) 40 | Folate (b) 30 | B-hCG 30 | Prolactin 30 |
| 7 | B-12 (b) 40 | HCV 80 | LH 80 | TSH 130 |
| 8 | Ferritin 70 | CA 19-9 40 | Testosterone 40 | B-12 (a) 40 |
| 9 | FT 4 70 | Progester-One 40 | TSH 130 | B-12 (b) 40 |
| 10 | | TSH 130 | Ferritin 70 | FT 4 70 |
| 11 | | B-12 (a) 40 | FT 4 70 | |
| 12 | | B-12 (b) 40 | | |
| 13 | | Ferritin 70 | | |
| 14 | | | | |
| 15 | | | | |
| 16 | | | | |
| 17 | | | | |
| 18 | | | | |
| 19 | | | | |

TABLE 11-continued

| SLOT # | INSTRUMENT 12A | INSTRUMENT 12B | INSTRUMENT 12C | INSTRUMENT 12D |
|---|---|---|---|---|
| 20 | | | | |
| 21 | | | | |
| 22 | | | | |
| 23 | | | | |
| 24 | | | | |
| 25 | | | | |
| TOTALS | 9/1280 | 12/1320 | 11/1350 | 10/1320 |

TABLE 12

| SLOT # | INSTRUMENT 12A | INSTRUMENT 12B | INSTRUMENT 12C | INSTRUMENT 12D |
|---|---|---|---|---|
| 1 | CEA 500 | CEA 500 | AFP 500 | AFP 220 |
| 2 | TSH 360 | FT 3 240 | FT 4 240 | HBSAg 400 |
| 3 | TT4 160 | HBsAb 200 | HBcAb 160 | HCV 240 |
| 4 | AFP 180 | HIV 1/2 80 | TT 3 120 | Estradiol 120 |
| 5 | | AFP 180 | CEA 250 | CEA 250 |
| 6 | | | | |
| 7 | | | | |
| 8 | | | | |
| 9 | | | | |
| 10 | | | | |
| 11 | | | | |
| 12 | | | | |
| 13 | | | | |
| 14 | | | | |
| 15 | | | | |
| 16 | | | | |
| 17 | | | | |
| 18 | | | | |
| 19 | | | | |
| 20 | | | | |
| 21 | | | | |
| 22 | | | | |
| 23 | | | | |
| 24 | | | | |
| 25 | | | | |
| TOTALS | 4/1200 | 5/1200 | 5/1270 | 5/1230 |

The allocation method can also provide a number of options for tailoring or modifying the method to meet particular needs. Some examples of such options follow.

It is possible to modify the allocation method to reduce or to eliminate use of partial reagent packs. In both the first and second passes described above, partial packs can be utilized to decrease reagent waste. By utilizing full reagent packs, additional tolerance and choices may be provided to both an algorithm that controls sample distribution and sample arrival. However, work load, i.e. reaction vessel utilization, distribution may continue to be performed with the actual test distribution list. If a sufficient number of open reagent slots are available for the operator to utilize partial packs, this may be a desirable option.

Another option permits redistribution of work load after the second pass described above is performed. An alternative approach is to save data generated by the first pass as a backup, distribute tests across the instruments 12A, 12B, 12C and 12D according the required test duplication percentage, and then perform load distribution again during the second pass. This level of complexity could be incorporated if desired by simulation results. However, redistributing tests and reaction vessel utilization in the second pass may, in some circumstances, degrade repeatability of the allocation method, and result in increased operator efforts and instrument 12A, 12B, 12C and 12D setup time when the test distribution profiles change.

It is possible to remove full reagent packs from the instruments 12A, 12B, 12C and 12D prior to performing test duplication across the instruments 12A, 12B, 12C and 12D. In some cases, only partial reagent packs are removed from the instruments 12A, 12B, 12C and 12D prior to test duplication of that same test. This can reduce an impact to the distributed work load, but may also provide a compromise step towards the concept presented the first discussed option. If a full or partial reagent pack satisfies the reaction vessel utilization specified by the duplication percentage for a given one of the instruments 12A, 12B, 12C and 12D, then surplus inventory on that instrument 12A, 12B, 12C and 12D may remain on that instrument 12A, 12B, 12C and 12D.

In another option, although the first pass of the test and load distributions described above start at the instrument 12A, 12B, 12C and 12D which is encountered first by a sample conveyed by the common sample supply, it is possible to start these distributions at any selected one of the instruments 12A, 12B, 12C and 12D within the system 10. Simulation results can be referenced and used in determining at which of the instruments 12A, 12B, 12C and 12D the distributions should begin.

In the first pass, test and load distributions are intentionally biased towards duplication (adding a test to the instruments 12A, 12B, 12C and 12D with the lowest kit repetition). Since this may increase redundant calibrations of at least one of the instruments 12A, 12B, 12C and 12D, this feature may be undesirable in some circumstances. However, this feature is a compromise step towards reaching the desired duplication percentage to increase throughput of the system 10. This step reduces an effect of the duplication percentage on load distribution. If reaction vessel utilization is redistributed after the second pass, then, in some instances, this feature should be turned off. It may be beneficial to reference simulation results when deciding whether to turn this feature off. The benefits provided by turning off the feature should be weighed against operator inconvenience of duplicate inventory and calibrations.

If desired, it is possible to adjust the test distribution profile which is assumed to be maximums. By increasing these maximums, additional tolerances and choices are provided. However, reaction vessel utilization distribution would continue to be performed with the actual test distribution list.

It is also possible to increase the duplication percentage. Performance advantages may be obtained by additional duplication. However these advantages need to be weighed against operator inconvenience of duplicate inventory and calibrations.

What is claimed is:

1. A method of allocating resources in a system comprising at least two instruments, the method comprising the steps of:

(a) generating a list of tests to be performed by the system within a reaction vessel, the list including a number of reaction vessels used in performing each test to be performed by the system in a given time period;

(b) sorting the list of tests according to the number of reaction vessels used in performing each test to be performed by the system in the given time period;

(c) determining a duplication percentage for the tests;

(d) comparing the duplication percentage with the sorted list of tests; and (e) duplicating resources associated with the tests across the at least two instruments based on the comparison of step (d) such that at least one of the tests is performed by at least two of the at least two instruments.

2. A method as defined in claim 1 further comprising the step of:

(f) distributing the tests across the at least two instruments such that the number of reaction vessels used in performing each test to be performed by the system in the given time period is positioned substantially evenly across the at least two instruments comprising the system.

3. A method as defined in claim 2 wherein step (e) is performed prior to step (f).

4. A method as defined in claim 2 wherein step (f) is performed prior to step (e).

5. A method as defined in claim 1 wherein the duplication percentage is about 30 percent.

6. A method as defined in claim 1 wherein the the duplicating step (e) comprises:

(i) obtaining the test that has the highest number of reaction vessels used in the given time period from the list generated in step (a);

(ii) duplicating resources associated with the test that has the highest number of reaction vessels used in the given time period across the at least two instruments based on the comparison of step (d) such that the test that has the highest number of reaction vessels used in the given time period is performed by at least two of the at least two instruments.

7. A method as defined in claim 1 wherein requirements of at least one of the steps are modifiable by an operator.

8. A method as defined in claim 1 further comprising the step of:

(f) distributing the tests across the at least two instruments such that the number of reaction vessels used in performing each test to be performed by the system in the given time period is positioned across the at least two instruments comprising the system.

* * * * *